United States Patent [19]

Gershoni

[11] Patent Number: 5,770,572
[45] Date of Patent: Jun. 23, 1998

[54] METHODS AND COMPOSITIONS USING MOLECULAR DECOYANTS FOR AMELIORATING THE UNDESIRED EFFECTS OF FOREIGN AGENTS WHICH BIND TO ENDOGENOUS RECEPTORS

[76] Inventor: Jonathan M. Gershoni, 297 Congressional La., Rockville, Md. 20251

[21] Appl. No.: 410,778

[22] PCT Filed: Aug. 30, 1988

[86] PCT No.: PCT/US88/02991

§ 371 Date: Jun. 30, 1989

§ 102(e) Date: Jun. 30, 1989

[87] PCT Pub. No.: WO89/01779

PCT Pub. Date: Mar. 9, 1989

[30] Foreign Application Priority Data

Aug. 30, 1987 [IL] Israel ............................................ 83687

[51] Int. Cl.$^6$ .......................... A61K 38/00; A61K 38/02; A61K 38/04

[52] U.S. Cl. ................................. 514/13; 514/2; 514/21; 530/326; 530/350

[58] Field of Search .................................... 530/326, 325, 530/327, 328, 329, 330, 350; 514/13, 21, 2

[56] References Cited

U.S. PATENT DOCUMENTS

| | | | |
|---|---|---|---|
| 4,761,371 | 8/1988 | Bell et al. | 435/68 |
| 5,126,433 | 6/1992 | Maddon et al. | 530/395 |

FOREIGN PATENT DOCUMENTS

| | | | |
|---|---|---|---|
| A-0 176 429 | 4/1986 | France | A61K 39/395 |
| 8801304 | 2/1988 | WIPO | C12Q 1/68 |

OTHER PUBLICATIONS

J. Cellular Biochemistry Supplement 16E, 1992 Abstract No. Q512–515.
Ward et al (1991) Nature 352:434.
Watanabe et al (1989) Nature 337:267.
Lentz (1985) Trends in NeuroSci. 82:360–364.
Moore, J. P. (1992) "Virions of Primary Human Immunodeficiency Virus Type 1 Isolates REsistant to Soluble CD4 (sCD4) Neutralization Differ in sCD4 Binding and Glycoprotein gp120 Retention from sCD4–Sensitive Isolates" J. Virology 66 (1): 235–243.
"Marshaling Recombinant DNA to Fight AIDs" in *Recombinant DNA*, second edition, Watson, J. D. et al, Scientific American Books, NY, 1992, pp. 485–509.
Daar, E.S. et al (1990) "High Concentration of Recombinant Soluble CD4 are Required to Neutralize Primary Human Immunodeficiency Virus Type 1 Isolates" Proc. Natl. Acad. Sci. USA 87: 6574–6578.
Goodman, B. (1995) "A Controversy That Will Not Die: The Role of HIV in Causing AIDs" The Scientist 9(6): 1, 6, 7.
Duesberg, P "Duesberg on AIDS Causation: The Culprit is Noncontagious Risk Factors" The Scientist 9(6): 12.

(List continued on next page.)

*Primary Examiner*—Ponnathapura Achutamurthy
*Attorney, Agent, or Firm*—Browdy and Neimark

[57] ABSTRACT

Molecular decoyants are chemical structures which functionally resemble an endogenous receptor. They may be used for the treatment of humans or other animals which have been subjected to a foreign agent which exerts an undesired effect only after first binding to that endogenous receptor. A decoyant is a fraction of an endogenous receptor which retains the essential elements of the binding site of the receptor for the foreign agent or is a synthetic or biosynthetic derivative thereof. The α184–200 amino acid sequence of *Torpedo californica* acetylcholine receptor is an example of a decoyant which protects against curarimimetic neurotoxins. Another example is the fraction of the CD4 receptor which retains the essential elements of the receptor for protection against HIV.

26 Claims, 7 Drawing Sheets

1) Synthetic oligonucleotides

```
41: 3'-GTCCACATCATTTGGGTCACAAAGGTCGCCGGAAGCTAGGG-5'
37: 3'-GATGTGGACGACGGGCCTGTGAGGCATGGACCTGACT-5'
```

2) Klenow fill-in

```
        41
5'_______________                    ________
        _______________ ||||||||||| _____________ 5'
                          37
```

3) Insertion into Sma site of pATH2:

```
                            CFX cleavage
                                |
                             ▼ 184              200
           I      E    G    R  W ──────────────► D
  5' CCC⌇⌇GGG  ATC  GAA  GGC  CGC ................TGA⌇⌇GGG
     ↑                                              ↑
     reconstituted Sma site                     termination
```

OTHER PUBLICATIONS

Gottlieb, A. A. "Pursuing HIV Alone as a Therapeutic Target has been a Faulty AIDS Research Strategy" The Scientist 9(6): 13.

Nucci et al (1991) Advanced Drug Delivery Reviews 6:133–151.

The Economist, Jan. 8th 1994 "AIDS Drugs Beyond Success".

Biochem. Soc. Trans., 1988, 16/2 (138–139) Gershoni: "Protein–Blot Analysis of Receptor–Ligand Interactions".

Proc. Natl. Acad. Sci. USA, vol. 83, pp. 3008–3011, May 1986, Nemnann et al.: "Mapping of the α–Bungarotoxin Binding Site Within the α–Subunit of the Acetylcholine Receptor".

Proc. Natl. Acad. Sci. USA, vol. 84, pp. 4318–4321, Jun. 1987, Gershoni: "Expression of the α–Bungarotoxin Binding Site of the Nicotinic Acetylcholine Receptor by *Escherichia coli* Transformants".

Proc. Natl. Acad. Sci. USA, vol. 80, pp. 4973–4977, Aug. 1983, Gershoni et al.: "Binding of α–Bungarotoxin to Isolated α–Subunit of the Acetylcholine Receptor of Torpedo Californica: Quantitative Analysis With Protein Blots".

Biochimica et Biophysica Acta 856 (1986), pp. 19–26, 1986, Gershoni et al.: "Protein Blot Analysis of Virus Receptors: Identification and Characterization of the Sendai Virus Receptor".

Electrophoresis 1987, vol. 8, pp. 428–431, Gershoni: "The Application of Ligand Overlay of Protein Blots to the Study of the Nicotinic Acelytcholine Receptor".

Analytical Biochemistry 131, pp. 1–15, 1983, Gershoni et al.: "Protein Blotting: Principles and Applications".

Proc. Natl. Acad. Sci. USA, vol. 81, pp. 2553–2557, Apr. 1984, Wilson et al.: "Binding of α–Bungarotoxin to Proteolytic Fragments of the α–Subunit of Torpedo Acetylcholine Receptor Analyzed By Protein Transfer on Positively Charged Membrane Filters".

Proc. Natl. Acad. Sci. USA, vol. 82, pp. 3490–3493, May 1985, Neumann et al.: "Antibodies to Synthetic Peptides as Probes for the Binding Site on the α–Subunit of the Acelytcholine Receptor".

Biochemical and Biophysical Research Communications, vol. 145, No. 2, pp. 810–816, Jun. 15, 1987, Mosckovitz, et al.: "Localization of Azidophencyclidine–Binding Site on the Nicotinic Acelytcholine Receptor α–Subunit".

The Journal of Biological Chemistry, vol. 263, No. 20, pp. 9933–9937, Jul. 15, 1988, Aronheim et al.: "Characterization of the Binding of α–Bungarotoxin to Bacterially Expressed Cholinergic Binding Sites".

Molecular Basis of Nerve Activity, Editous: Changeux et at., Walter de Grayter & Co. Berlin, FRG, 1985, pp. 303–313, Gershoni: "Protein–Blot Analysis of the Nicotinic Acetylcholine Receptor".

The Journal of Biological Chemistry, vol. 263, pp. 1017–1022, 1988, Mosckovitz et al.: "Three Possible Disulfides in the Acetylcholine Receptor α–Subunit".

Proc. Natl. Acad. Sci. USA, vol. 85, pp. 4087–4089, Jun. 1988, Gershoni et al.: "Molecular Decoys: Ligand–Binding Recombinant Proteins Protect Mice From Curarimimetic Neurotoxins".

Science, vol. 238, Dec. 18, 1987, pp. 1704–1707, Smith et al.: "Blocking of HIV–1 Infectivity By A Soluble, Secreted Form of the CD4 Antigen".

Nature, vol. 331, Jan. 7, 1988, pp. 76–78, Fisher et al.: "HIV Infection is Blocked in Vitro By Recombinant Soluble CD4".

Nature, vol. 331, Jan. 7, 1988, pp. 78–81, Hussey et al.: "A Soluble CD4 Protein Selectively Inhibits HIV Replication and Syncytiun Formation".

Nature, vol. 331, Jan. 7, 1988, pp. 82–84, Dean et al.: "A Soluble Form of CD4 (T4) Protein Inhibits AIDS Virus Infection".

Nature, vol. 331, Jan. 7, 1988, pp. 84–86, Traunecker et al.: "Soluble CD4 Molecules Neutralize Human Immunodeficiency Virus Type 1".

Proc. Natl. Acad. Sci. USA, vol. 85, pp. 6102–6106, Aug. 1988, Richardson et al.: "Binding Site For Human Immunodeficiency Virus Coat Protein gp120 is Located in the $NH_2$–Terminal Region of T4 (CD4) and Requires the Intact Variable–Region–Like Domain".

Chemical Abstract, vol. 106, issued 27 Apr. 1987 (Columbus, Ohio, USA) "CD4 Receptor Binding Peptides that Block HIV Infectivity Cause Human Monocyte Chemotaxis. Relationship to Vasoactive Intestinal Polypeptides." (Ruff) Abstract No. 136804e.

Chemical Abstract, vol. 103, issued 16 Sep. 1985 (Columbus, Ohio USA) "Molecular Comparison of–and and Adrenergic Receptors Suggests that these Proteins are Structurally Related Isoreceptors." (Shreeve) Abstract No. 82334u.

Chemical Abstract, vol. 103, issued 19 Aug. 1985 (Columbus, Ohio USA) Pseudomonas Pili. Studies on Antigenic Determinants and Mammalian Cell Receptors. (paranchych) abstract No. 50925w.

Chemical Abstract, vol. 105, issued 21 Jul. 1986 (Columbus, Ohio USA) "Pertussis Vaccine Reduces Agonist Binding to the Rat Heart Muscarinic Receptor and its Guanine Nucleotide Modulation." (Anguilar) Abstract No. 19282b.

Chemical Abstract, vol. 105, issued 1 Sep. 1986 (Columbus, Ohio USA) "Saliva Interacting Proteins of S. Mutans: Puridicaiton, Characterization and Use in Immunization Studies of a 74K Cell Surface Saliva Receptor (74K SR)." (Klein) Abstract No. 75498p.

Biochemistry, vol. 26, Jun. 16, 1987, pp. 3261–3266, American Chemical Society; S. Ralston et al: "Synthetic peptides used to locate the alpha–bungarotoxin binding site and immunogenic regions on alpha subunits of the nicotinic acetylcholine receptor".

Proc. Natl. Acad. Sci. USA, vol. 82, Dec. 1985, pp. 8790–8794; P.T. Wilson et al: "Determination of the primary amino acid sequence specifying the alpha–bungarotoxin binding site on the alpha subunit of the acetylcholine receptor from torpedo californica".

Internat. Workshop on Structural and Functional Aspects of the Cholinergic Sympose Aug. 30–Sep. 4, 1987, pp. 74–75; J.M. Gershoni et al: "Correlating structure with function of the cholinergic binding site".

Changeux et al (1987) TIPS 8:459–465.

Dennis et al (1986) FEBS Lett. 207(2):243–249.

Eppstein et al (1985) Nature 318:663–665.

Lentz et al (1987) *Proteins: Structure, Function and Genetics* 2:298–307.

Leung et al (1987) Nature 330:537–543.

McDaniel et al (1987) J. Protein Chem. 6(5):455–461.

Rert et al (1986) PNAS USA 83:9254–9258.

Pierschbacher et al (1984) PNAS USA 81:5985–5988.

Ruff et al FEBS Lett 211:17–22 (1987).

METHODS AND COMPOSITIONS USING MOLECULAR DECOYANTS FOR AMELIORATING THE UNDESIRED EFFECTS OF FOREIGN AGENTS WHICH BIND TO ENDOGENOUS RECEPTORS

FIELD OF THE INVENTION

The present invention relates to substances useful for the treatment of animals, including humans, which have been subjected to a foreign agent, which agent exerts an undesired effect only after first binding to an endogenous receptor. More particularly, the present invention relates to such substances, and methods of use thereof, which are directly or indirectly derived from the natural endogenous receptor.

BACKGROUND OF THE INVENTION

In order to exert their action in a living body, many pathogenic and toxic agents, such as viruses, bacteria and also toxins and poisons, become attached to specific binding sites, e.g., to cell surface receptors. Such binding phenomena may be necessary as a first step in viral infectivity or may be the essence of toxic inactivation of a critical physiological function. A receptor is a cellular component that interacts with a specific ligand. Ligands classified as agonists, when bound to their receptors, activate an effector system and trigger a bioresponse. Ligands classified as antagonists depress receptors or inhibit the action of the agonist. When, for example, cobra venom or curare is attached to a cholinergic receptor, the binding of acetylcholine is prevented. Prevention of such formation of certain ligand-receptor complexes should be beneficial in combatting the deleterious effects of the pathogenic or toxic agent.

Prevention of complex formation can be achieved via a number of basically different approaches. For example, the generation of anti-toxin antisera has proven to be a useful approach in the treatment of snake bites. Immunological inactivation of viruses and bacteria is the essence of vaccination. In both of these cases the infiltrating substance is intercepted by highly stereospecific immunoglobulins which in turn prevent the substance from reaching its target of action.

Alternatively, a different approach has recently been suggested according to which an analogue of the foreign material is used to preoccupy the host receptor binding site, and thus viruses or bacteria are prevented from associating with the tissue they normally would infect.

These known approaches suffer certain basic drawbacks. Immunological inactivation is "ligand-specific". Furthermore, many bacteria and viruses have the capability of periodically modifying their immunogenic epitopes by random mutations and recombination processes, thereby rendering the immunoglobulin ineffective. The use of ligand analogues is "receptor-specific". However, by definition, such analogues occupy the receptor preventing its functionability.

The present invention employs a novel approach to the problem of prevention of formation of such ligand-receptor complexes which approach is "receptor-specific" yet does not prevent the functionability of the native receptor.

SUMMARY OF THE INVENTION

It is an object of the present invention to obviate the drawbacks of the prior art.

It is a further object of the present invention to provide a novel approach for the prevention of formation of ligand-receptor complexes which approach is "receptor-specific" yet does not prevent the functionability of the receptor sites.

It is another object of the present invention to provide molecular decoyants which are not substantially larger than the molecular structure of the ligand binding site in the native receptor and which can be used to bind pathogenic or toxic agents in vivo in a "target-specific" manner.

It is yet another object of the present invention to provide substances which are small enough as to be substantially non-immunogenic and which act as decoyants in vivo to compete with the natural binding sites and intercept the specific ligands and inactivate them.

It is still a further object of the present invention to provide a method for the treatment of animals, including humans, which have been subjected to foreign agents which exert an undesired effect only after first binding to an endogenous receptor.

It is still another object of the present invention to provide such a-method by administering a molecular decoyant which mimics the functional attributes of the binding site of the endogenous receptor.

These and other objects of the present invention will be further understood after consideration of the following detailed description of preferred embodiments in conjunction with the attached drawings.

The novel solution to the problem of prevention of formation of ligand-receptor complexes, when the ligand is a foreign agent which exerts an undesired effect by specifically associating with an endogenous receptor, involves the identification of the molecular structure of the ligand binding site in the native receptor and the production of mimic ligand binding sites. These sites can be used in vivo to bind toxins or viruses or any other foreign agent in a "target-specific manner". Thus, the mimic ligand binding sites of the present invention compete in the animal's body with natural binding sites, thus acting as decoys. Such substances have been denominated "molecular decoyants" by the present inventor.

It is believed that natural receptors are rather large structures, comprising some hundreds of amino acids, and can be as large as a molecular weight of about 250,000. The specific binding site, however, is much smaller and this opens up the possibility of preparing artificial, synthetic binding sites, which are effective in binding specific viruses, bacteria, toxins, etc., yet which comprise a much smaller number of amino acids, preferably less than 100, and which have therefore a considerably lower molecular weight and thus a correspondingly lower immunogenicity. It has been found possible to prepare such binding-site-mimicking molecular decoyants which are adapted to bind specific ligands with a size on the order of about 20 amino acids. Such rather small peptide structures can be prepared by physically dividing the endogenous receptor or they can be prepared synthetically by the preparative procedures of peptide chemistry, such as Merrifield synthesis, or by genetic engineering. This opens up the possibility of large scale production of such specific polypeptide structures and their use as active materials in the treatment of animals subjected to pathogenic or toxic agents.

Since molecular decoyants bind to the ligand at the very site required by the ligand to bind with the endogenous receptor required to exert its undesired effect, this site cannot be changed by the ligand without deactivating itself. Thus, decoyants are much more reliable than immunoglobulins and have a long term effect.

The present invention is of a very wide applicability as molecular decoyants specific to a wide variety of ligands can be produced. The present invention includes prophylactic as well as therapeutic compositions which contain the active molecular decoyant structures in an adequate concentration and quantity.

BRIEF DESCRIPTION OF THE DRAWINGS

FIG. 2 shows the results of the separation on polyacrylamide gels of various samples of an R4137 clone cultured for induction of the trpE fusion protein. The cells were either solubilized in sample buffer (T) or sonicated in high salt buffer (500 mM) and centrifuged. The supernatant ($S_1$) contained 40–60% of the fusion protein as did the pellet (Pi). The pellet was further extracted with water to generate a supernatant ($S_2$) which contained some 15% of the original fusion protein content and a pellet ($P_2$). After polyacrylamide gel electrophoresis (PAGE), the samples were either stained with Coomassie brilliant blue (top) or blotted and overlayed with $^{125}$I-labeled α-bungarotoxin (BTX) followed by autoradiography (bottom). The arrowheads indicate the position of the fusion protein. Numbers indicate relative molecular mass in kDa.

FIG. 4 is a graph showing the Scatchard analysis of toxin binding to R4137. After incubation with different concentrations of $^{125}$I-labeled BTX until equilibrium was achieved (30 min), net bound BTX was determined by adding a 1,000 fold excess of nonradioactive BTX and the bound versus the free toxin for each point was calculated.

FIG. 5 is a graph showing competition of BTX binding. The percent of $^{125}$I-labeled BTX ($2 \cdot 10^{-8}$M) is plotted after mixing with ever increasing concentrations of: non-labeled BTX (●), cobratoxin (△), decamethonium (◊), d-tubocurarine (○), NaCl (□), carbamylcholine (x) or glycine ( | ). The mixtures were incubated with equal amounts of R4137 for 30 min at 25° C. and the net amount of bound radioactive toxin was determined.

FIG. 7 is a graph showing the effect of R4137 on the survival rate of d-tubocurarine injected mice. Two groups of Balb/C mice (35 in each) were injected with either pATH2 or R4137 (approx. 3 nmole BTX binding sites/mouse) intraperitoneally. Five minutes later the mice were given d-tubocurarine (approx. 15 nmole, 9 µg/mouse, subcutaneously). The number of survivors as a function of time after the injection of toxin is shown (the data are derived from experiments 2 and 3 of Table 1).

DETAILED DESCRIPTION OF PREFERRED EMBODIMENTS

While the present invention is applicable to molecular decoyants which mimic the binding site of any endogenous receptor, it will be discussed in detail with respect to the cholinergic binding site. It is known that α-bungarotoxin (BTX), which is a snake venom α-neurotoxin, exerts its toxic effect by blocking the binding of cholinergic ligands to the nicotinic acetylcholine receptor (AcChoR).

The neuro-muscular junction is the site where nerves meet with muscle fibers. The point of contact is the synapse and is characterized by the fact that the nerve and muscle are not actually physically connected, but rather form a chemical junction. When the nerve pulse reaches the tip of the axon, acetylcholine, the neurotransmitter, is secreted into the gap between the nerve and muscle, i.e., "the synaptic cleft". The acetylcholine is bound by its receptor which is situated on the extracellular membrane of the muscle, the post-synaptic side of the junction. The binding of two molecules of acetylcholine to their receptor causes an ion-channel to open, the membrane to depolarize and eventually leads to muscle contraction.

BTX is an antagonist which binds to AcChoR, thereby preventing acetylcholine from reaching its receptor and preventing muscle contraction. To make a molecular decoyant for the treatment of animals subjected to BTX, one must first identify the particular BTX binding site. The preferred method for doing this is by means of ligand overlay of protein blots. Once the binding site is identified, the minimal sequence may be produced. Upon the administration of such a sequence, the decoy will mimic the binding site and bind with BTX, thereby blocking the undesired activity of the toxin.

The specific binding site for BTX on the AcChoR is known to be situated on the α-subunit thereof. The minimal essential elements of the binding site which will still permit selective and specific binding of reasonable affinity to BTX may be further identified by means of protein blotting. The techniques of protein blotting are discussed in detail in Gershoni, "Protein Blotting: A Manual" in *Methods of Biochemical Analysis*, edited by David Glick, John Wiley and Sons, vol. 33, pp. 1–55, 1988, the entire contents of which are hereby incorporated by reference. The process involves transferring resolved polypeptides from chromatographic gels to immobilizing matrices.

BTX is a polypeptide toxin (74 amino acid residues) which can be iodinated and binds the receptor with an affinity of $K_D=10^{-11}$M. Purified AcChoR is subjected to polyacrylamide gel electrophoresis (PAGE) under mild denaturation without boiling of the sample and use of lithium dodecyl sulfate, instead of sodium dodecyl sulfate (SDS). Blots are then prepared and probed with $^{125}$I-labelled BTX. Such experiments show that the α-subunit of the AcChoR is labelled (Gershoni et al, "Binding of α-Bungarotoxin to Isolated α-Subunit of the Acetylcholine Receptor of *Tornedo californica*: Quantitative Analysis with Protein Blots", *Proc. Natl. Acad. Sci. (USA)*, 80: 493–4977 (1983)). The α-subunit is then proteolysed and then protein blots thereof probed with alkaline-phosphatase hydrazide, concanavalin-A, BTX and sequence specific antibodies which together have allowed the mapping of the toxic binding site to the region α-160-330 and more particularly α-160-210 and even more specifically to the region α-180-200 (see Neumann et al, "Mapping of the α-Bungarotoxin Binding Site with the α-Subunit of the Acetylcholine Receptor", *Proc. Natl, Acad. Sci. (USA)*, 83:3008–3011 (1986), the entire contents of which are hereby incorporated by reference).

In order to determine the cholinergic binding site more particularly, a number of synthetic peptides were prepared and their capacity to bind cholinergic ligands was assessed.

Of the many peptides tested the only ones that were capable of BTX binding included the sequence α-185-196. This peptide was found to have low affinity ($10^{-5}$M) yet highly specific BTX binding ability. Higher affinity ($10^{-7}$M) was found for the sequence α-173-204.

BTX-binding sequences can also be produced by recombinant DNA techniques, sub-clones of cDNA of α-sub-units of mouse or Torpedo californica were prepared using expression vectors. The trpE fusion vector pATH2 was used. Restriction fragments of the plasmid p42, a cDNA clone of the α-subunit of Torpedo californica AcChoR, were purified on 1% agarose gels. Preparative quantities of plasmids were obtained, and ligations in transformations of E. coli strain HB101 were performed by the methods of Maniatis et al., "Molecular Cloning: A Laboratory Manual", Cold Spring Harbor Laboratory, Cold Spring Harbor, N.Y., 1982. By such means fusion proteins were prepared in E. coli transformants (Gershoni, "Expression of the α-Bungarotoxin Binding Site of the Nicotinic Acetylcholine Receptor by Escherichia coli Transformants", Proc. Natl. Acad. sci. (USA), 84, 4318–4321 (1987), the entire contents of which are hereby incorporated by reference). These fusion proteins were shown to specifically bind BTX (affinity: $10^{-7}$M). Thus, for example, bacterially expressed proteins containing α-166-200 bind toxin whereas those expressing α-201-315 do not.

Figure 1:
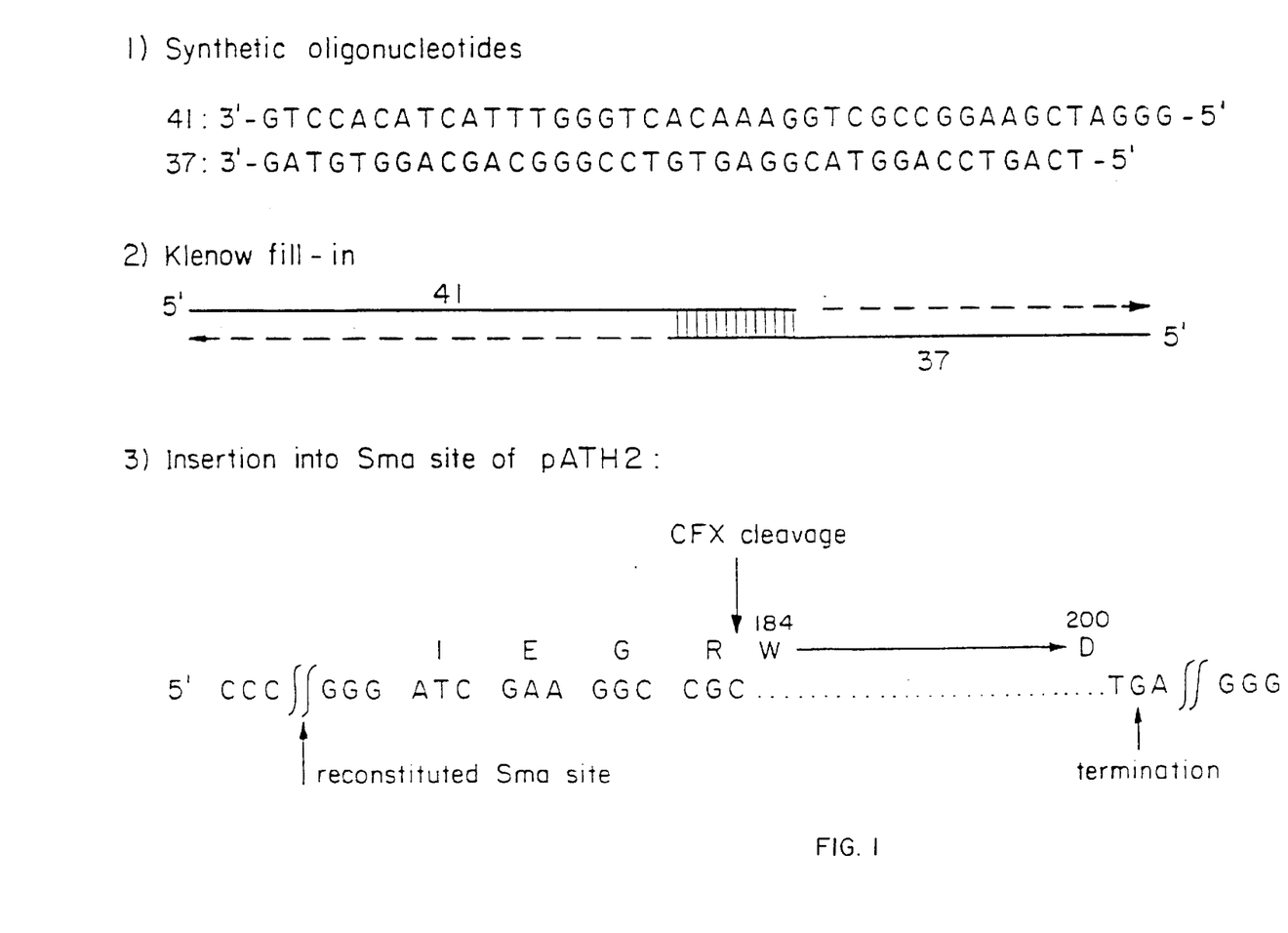
FIG. 1 shows the process steps for obtaining the 17 amino acid sequence WKHWVYYTCCPDTPYLD by recombinant DNA technology.

Two oligonucleotides were prepared as described in FIG. 1(1). They were designed using bacterially preferred codons to code for the amino acid sequence: Gly-Ile-Glu-Gly-Arg-Trp-Lys-His-Trp-Val-Tyr-Tyr-Thr-Cys-Cys-Pro-Asp-Thr-Pro-Tyr-Leu-Asp, which includes α184-200 of Torpedo californica AcChoR as well as a pentapeptide introduced N-terminal to residue W184. The first glycine is the result of the trinucleotide dGGG which is necessary for the maintenance of a functional SmaI site. The following sequence IEGR is the specific cleavage site for the coagulation factor Xa (CFX). Thus the expressed fusion protein becomes cleavable with this enzyme thereby enabling the eventual release of the site of interest, i.e., the 17 amino acid sequence: WKHWVYYTCCPDTPYLD. The two oligonucleotides were mixed at a ratio of 1:1 heated together and allowed to anneal forming a 9-base pair duplex. The complementary strands were then enzymatically "filled in" using Klenow polymerase.(1μl; 5 units), as shown in FIG. 1(2), after which the DNA was phenol-extracted and precipitated in ethanol using glycogen as a carrier. The construct was then ligated with SmaI-cut, purified pATH2 expression vector. The ligated vectors were used to transform E. coli strain HB101, all in accordance with the techniques described in Aronheim et al, "Characterization of the Binding of α-Bungarotoxin to Bacterially-Expressed Cholinergic Binding Sites", J. Biol. Chem., 263, 20:9933–9937 (1988), the entire contents of which are hereby incorporated by reference.

Figure 2:
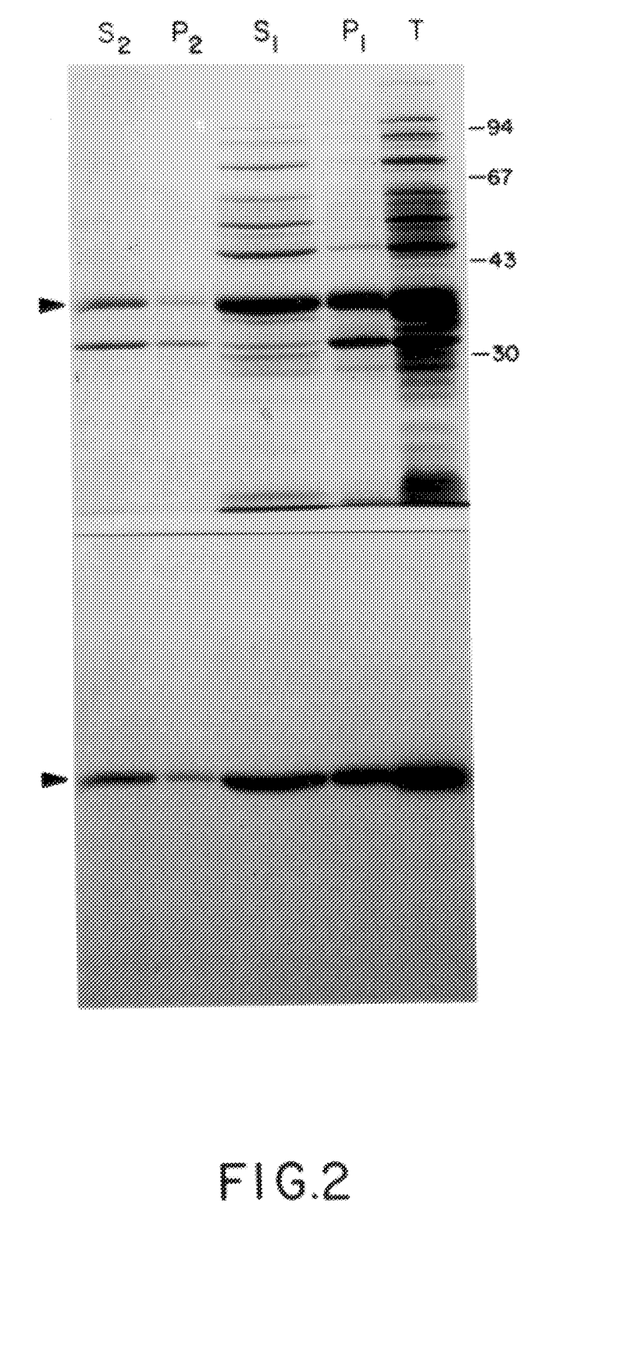

The transformed bacterial clones which contained the insert in proper orientation were selected by, $^{125}$I-labeled BTX overlay of colony-blots. These transformants were found to produce an efficient toxin-binding fusion-protein (36kDa designated R4137, FIG. 2). R4137 could be highly enriched by sonicating the transformed cells in phosphate buffer+500 mM salt. Centrifugation resulted in a pellet which contained 40–60% of the total R4137 and little more (FIG. 2, $P_1$). This pellet could be extracted with water to produce a soluble fraction which was predominantly R4137 (FIG. 2, $S_2$).

Figure 3A:
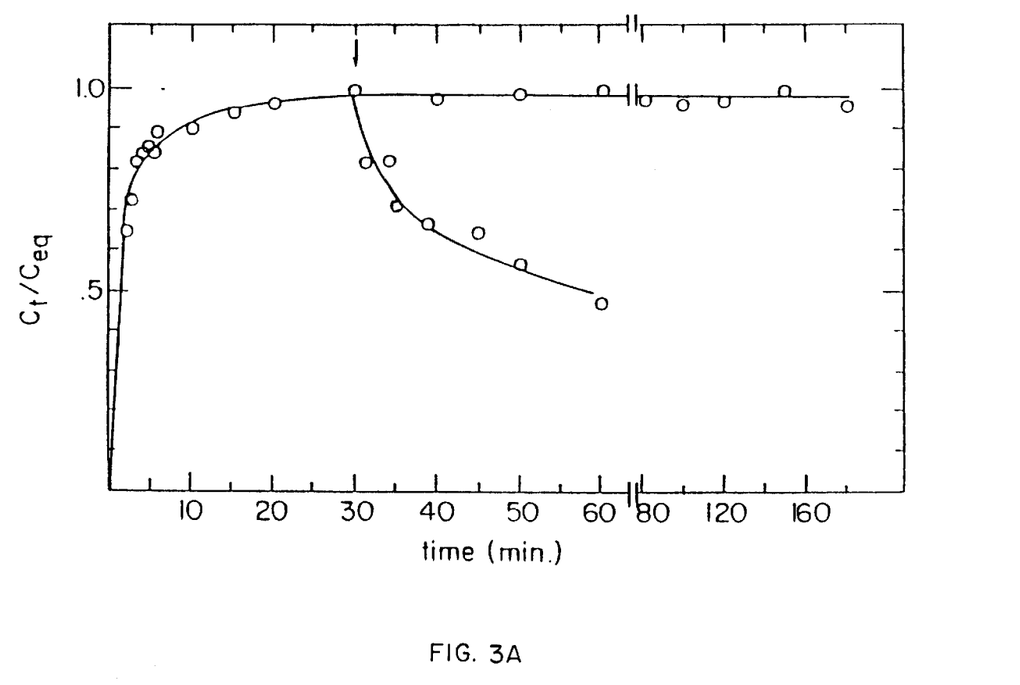
FIG. 3 is a graph showing the concentration of bound toxin at specific times ($C_t$) divided by that reached at equilibrium ($C_{eq}$) after incubation of R4137 with $^{125}$I-labeled BTX for different periods of time as indicated. The concentrations were measured after applying aliquots to positively charged membrane filter discs. The time was measured in minutes in panel A or seconds in panel B.
Figure 3B:
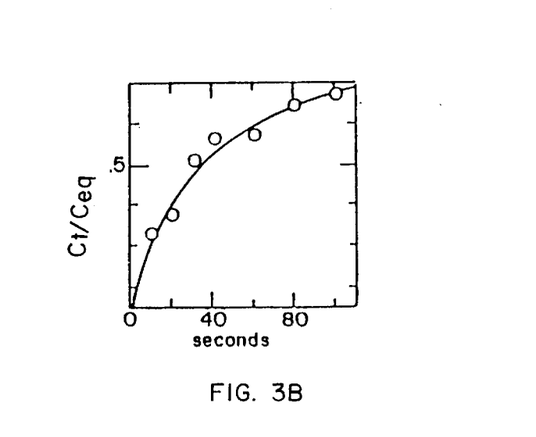
Figure 4:
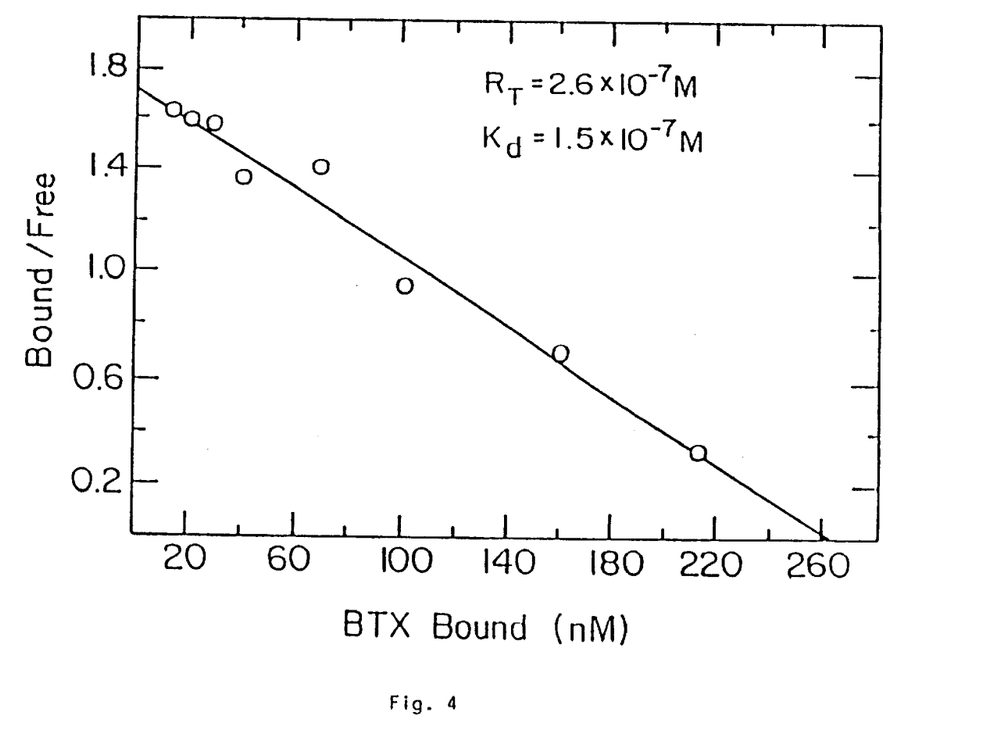
Figure 5:
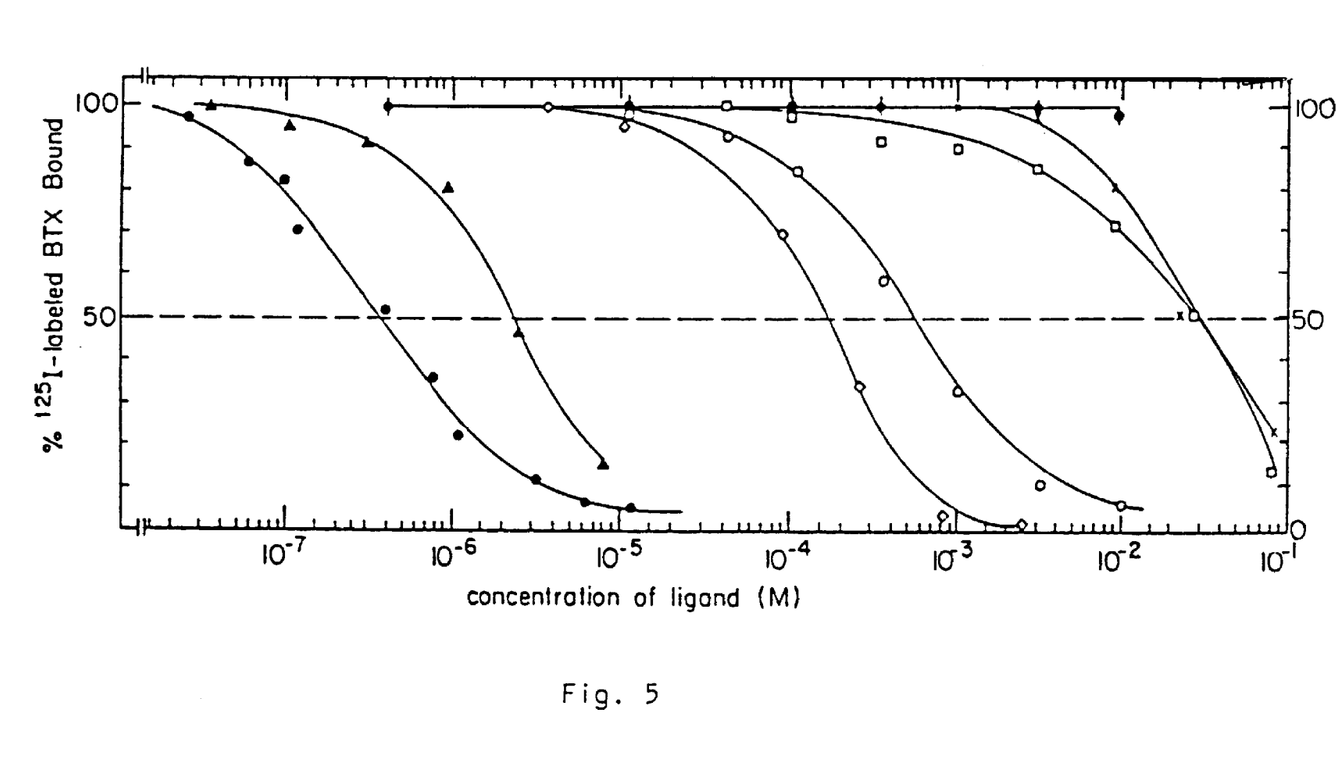

The R4137 in the $S_2$ fraction was biochemically characterized by measurement of toxin binding thereto in accordance with the techniques described in Gershoni et al, "Molecular Decoys: Ligand-Binding Recombinant Proteins Protect Mice from Curarimimetic Neurotoxins", Proc. Natl. Acad. Sci (USA), 85, 4087–4089 (1988), the entire contents of which are hereby incorporated by reference. In essence, aliquots of $S_2$ were incubated with $^{125}$I-labelled BTX. Then the mixture was filtered through a charge modified membrane filter to separate the bound versus free toxin. The filters were then counted for radioactivity. Using this technique it was found that BTX associates with R4137 in a pseudo first order kinetic which reaches 50% completion within 40 sec and about 90% completion after 6 min (FIG. 3). Measurements of toxin binding at equilibrium (30 min reaction) showed that toxin bound to R4137 with a $K_{D}$=1.2× $10^{-7}$M (FIG. 4). This binding could be competed with other cholinergic ligands with a progression of efficiencies which is similar to that known for the intact receptor (FIG. 5).

Accordingly, R4137 demonstrates that the 17 amino acid sequence: α-184-Trp-Lys-His-Trp-Val-Tyr-Tyr-Thr-Cys-Cys-Pro-Asp-Thr-Pro-Tyr-Leu-Asp-200 is sufficient for BTX binding. Although this binding is appreciably less than that of the intact receptor, it does resemble the binding characteristics of the complete α-subunit (437 amino acids) of AcChoR.

Figure 6A:
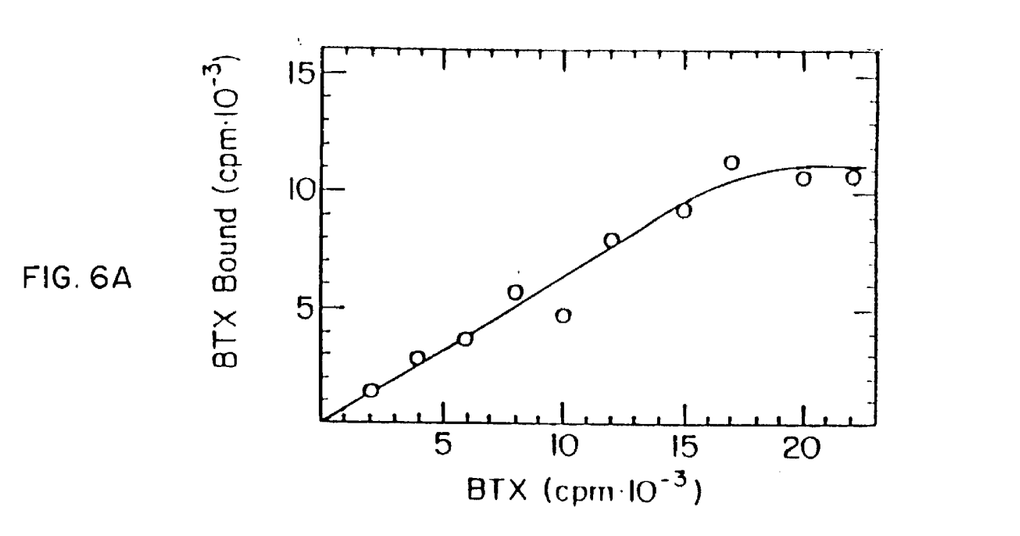
FIG. 6A is a graph plotting the amount of bound $^{125}$I-labeled BTX as a function of the total amount of $^{125}$I-labeled BTX applied to a concanavalin-A column having AcChoR immobilized thereon.
Figure 6B:
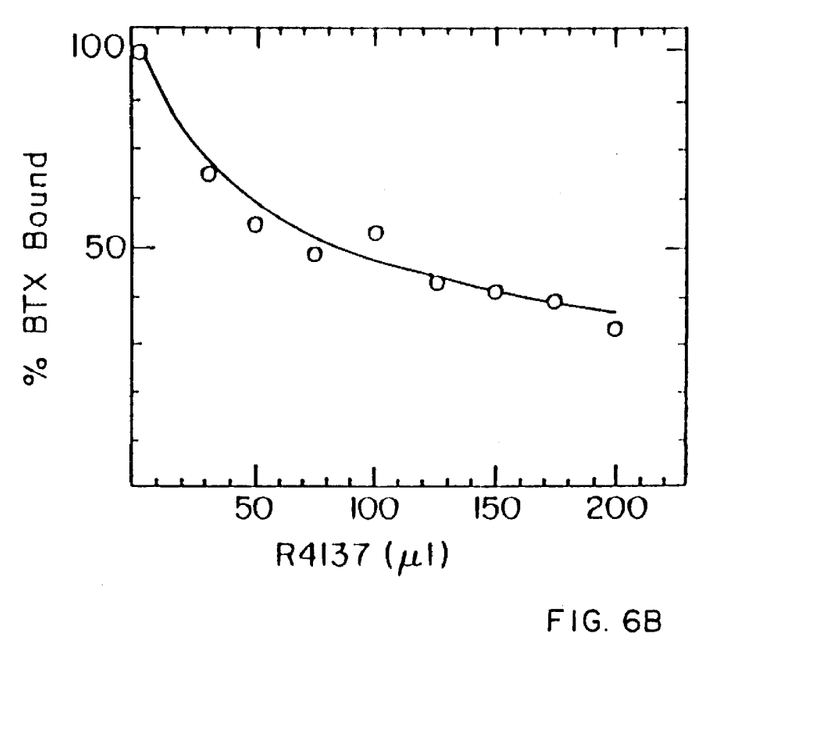
FIG. 6B is a graph plotting the amount of bound $^{125}$I-labeled BTX on a concanavalin-A column having AcChoR immobilized thereon as a function of the amount of R4137 applied to the column after different amounts of R4137 and constant amounts of $^{125}$I-labeled BTX were applied thereto.

In order to establish whether R4137 could be used as a treatment for animals which have been subjected to a neurotoxin, an experiment was conducted to establish that R4137 can compete against intact AcChoR for a common and limiting pool of BTX. In order to do this, one must not only separate bound BTX from free, but one must also distinguish between AcChoR-bound versus R4137-bound toxin. In order to do so, AcChoR was first bound to a concanavalin-A column. This was found to have little or no effect on toxin binding (FIG. 6A). Then such immobilized AcChoR was mixed with different concentrations of R4137 and constant amounts of $^{125}$I-labelled-BTX. Afterwards, the columns were washed by repeated centrifugation/resuspension and the amount of radioactivity associated with the column was determined. As can be seen in (FIG. 6B), R4137 effectively competes for BTX against AcChoR.

Figure 7:
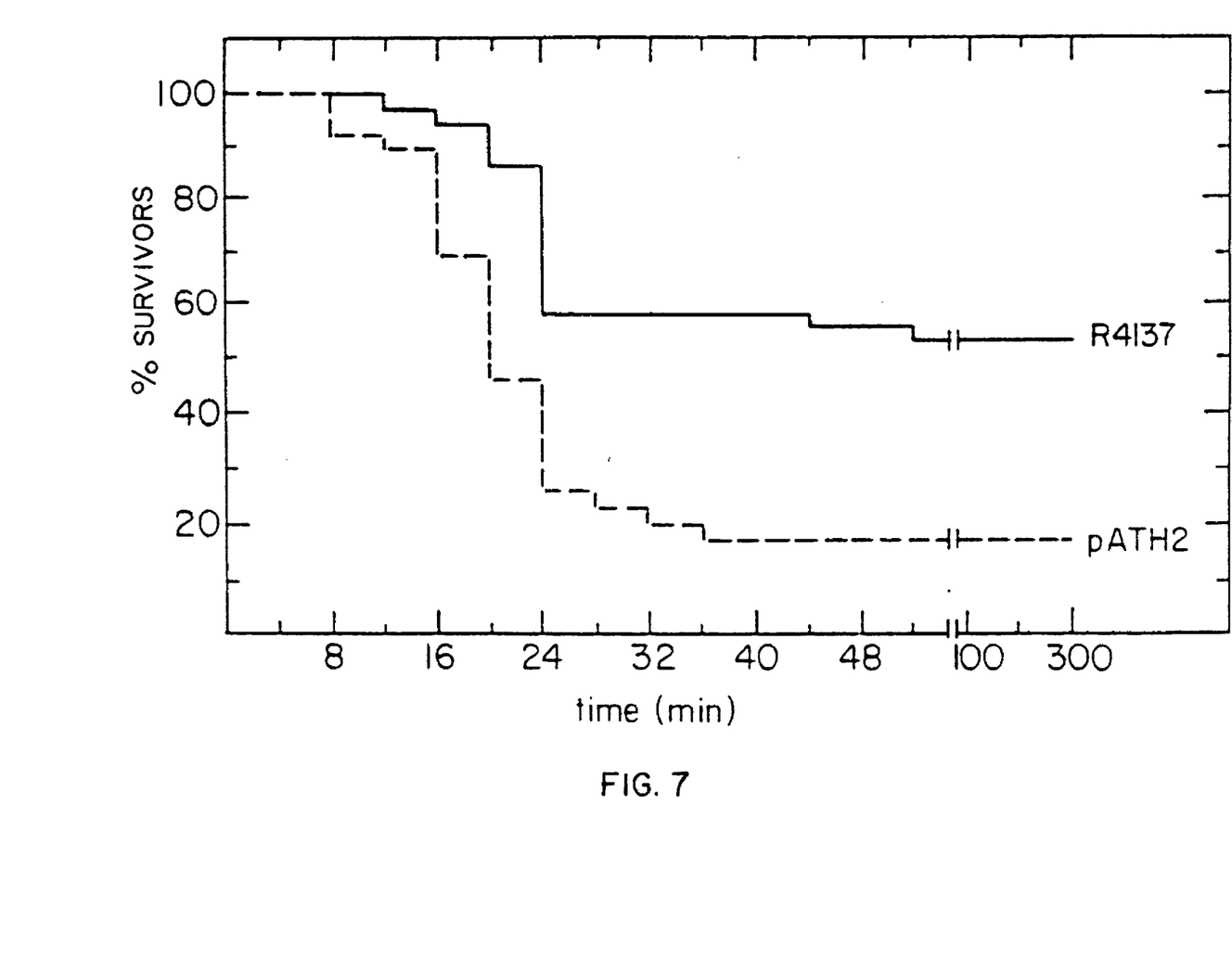

Finally, R4137 was tested for competition with AcChoR in vivo. Male and female mice (approximately 5 weeks, 20–25g), both inbred (Balb/C) and outbred (CD1) strains, were first injected intraperitoneally with R4137 or a placebo-a similar fraction derived from bacteria transformed with the unmodified vector pATH2 (these cells have no toxin-binding capacity). Five minutes later all the mice were challenged with various amount of d-tubocurarine or α-cobratoxin (CTX). The dose was gauged to cause 80% death of untreated mice. The toxins were administered by subcutaneous injection to the nape of the necks of the animals. The animals were observed and the number of deaths during the course of two hours after the toxin injection was recorded. The results are shown in Table 1. As shown in FIG. 7 the survival rate of the R4137 treated mice is markedly improved over the control and the absolute number of recoveries is at least 300% better than those that were given the placebo.

TABLE 1

| Exp. | Bacterial protein (i.p.) | Strain | Sex | Toxin (s.c.) | Dose mg/kg | No. of mice | Survivors |
|---|---|---|---|---|---|---|---|
| 1 | pATH2 | Balb/C | M | Tubo | 0.40 | 10 | 0 |
|   | R4137 |        |   |      |      | 10 | 3 |
| 2 | pATH2 | Balb/C | M | Tubo | 0.36 | 10 | 1 |
|   | R4137 |        |   |      |      | 10 | 7 |
| 3 | pATH2 | Balb/C | M | Tubo | 0.36 | 25 | 5 |
|   | R4137 |        |   |      |      | 25 | 12 |
| 4 | pATH2 | CD1    | M | Tubo | 0.36 | 37 | 10 |
|   | R4137 |        |   |      |      | 38 | 21 |

TABLE 1-continued

| Exp. | Bacterial protein (i.p.) | Strain | Sex | Toxin (s.c.) | Dose mg/kg | No. of mice | Survivors |
|---|---|---|---|---|---|---|---|
| 5 | pATH2 | CD1 | F | Tubo | 0.29 | 20 | 6 |
|   | R4137 |   |   |   |   | 20 | 15 |
| 6 | pATH2 | CD1 | M | CTX | 0.15 | 10 | 1 |
|   | R4137 |   |   |   |   | 10 | 10 |
| 7 | pATH2 | CD1 | M | CTX | 0.15 | 21 | 6 |
|   | R4137 |   |   |   |   | 20 | 12 |

A further experiment was carried out where mice were first injected with a lethal dose of cobra toxin and one hour later given either a placebo or the cholinergic decoyant. The animals which received the placebo all died, whereas the decoy-treated animals were dramatically protected (90% survival). The results are shown in Table 2. It should be understood that the same receptor site is involved with all of BTX, CTX and d-tubocurarine as well as decamethonium and rabies-virus.

TABLE 2

| Material injected | Time after toxin (minutes) | Survivors |
|---|---|---|
| R4137 (decoyant) | 30 | 6/10 |
|   | 60 | 9/10 |
|   | 90 | 6/7 |
| pATH (placebo) | 60 | 0/10 |

The fact that R4137 has been proven to be a decoyant against toxin is only a case in point for the general claim of molecular decoyants as therapeutic agents. In the specific case of the AcChoR, R4137, or improved versions of this molecular decoyant, can serve as an antidote against cobra-like snake bites by specifically intercepting the α-toxin constituent of these venoms. In addition, d-tubocurarine is routinely used in surgery as a neuro-muscular blocking agent and a decoyant based on R4137 could be extremely useful as its antidote. This utility is of particular importance as the use of ligand analogues as described in the prior art would be as detrimental as the blockers themselves. Moreover, it has recently been demonstrated that rabies-virus specifically binds AcChoR and that its binding can be competed against d-tubocurarine or BTX (Lentz et al., *Science*, 215, 182–184 (1982)). Thus, a decoyant based on R4137 will also provide therapeutic affects in the treatment of rabies.

It should be understood that R4137 is but an intermediate tool which, by its genetic manipulation or chemical processing, would allow those of ordinary skill in the art to design even more efficient cholinergic decoyants. Thus, the present invention is intended to include not only the specific 17 amino acid sequence of R4137, but variations and derivatives thereof which maintain, and preferably improve, its functional or pharmacological characteristics. For example, modified peptide sequences can be readily prepared and tested by routine techniques for preferred toxin-binding characteristics so as to more effectively compete against the native receptor. Such modification may involve substitution, deletion or insertion of amino acids or their chemical modification. For example, longer lived decoyants may be obtained in this manner. As enzymatic degradation of the decoyants in vivo may cause some decoyants to be relatively short-lived, one method of preventing such degradation would be by making synthetic peptides containing d-amino acids. Alternatively, based on the fusion-protein blueprint, organic molecules, i.e., not proteinaceous, can be designed so as to satisfy the physico-chemical requirements of a decoyant which must form a functional interface with the toxin.

It should further be understood that the decoyants of the present invention can be modified by extending the polypeptide or by adding specific chemical moieties intended to aid in drug design or to permit the decoyants to be used for additional utilities. One such modification would be to extend the polypeptide by moieties intended to affect solubility, e.g., by the addition of a hydrophilic residue, such as serine, or a charged residue, such as glutamic acid. Furthermore, the decoyant could be extended for the purpose of stabilization and preservation of a desired conformation, such as by adding cysteine residues for the formation of disulfide bridges.

Another reason to modify the decoyants would be to make the decoyant detectable, even after administration. This might be done by radioiodination with a radioactive iodine isotope, directly, or by adding tyrosine for subsequent radio-iodination. Such detectable decoyants could be used to detect the presence and/or location of specified pathogenic agents or toxins. For example, detection of an accumulation of R4137 in the area of a dog bite would indicate the presence of rabies-virus. Thus, such detectable decoyants could be used for the selective detection and mapping of given foreign agents or for diagnosis of the invasion of such an agent.

A further reason for modifying decoyants would be for accelerated clearance of the conjugated foreign agent from the body. For example, a decoyant linked to an asialoglyco-moiety would be expected to be cleared by the liver. Thus, for example, a decoyant mimicking the receptor site of an anti-cancer chemotherapeutic agent and containing such an asialoglyco-moiety, or any other moiety which would aid in its clearance, could be used to inactivate and quickly remove excess chemotherapeutic agent after the therapy is completed in order to reduce side effects.

Proof of the effectiveness of R4137 as a decoyant against toxin in vivo establishes the operability of the general concept of the present invention. Accordingly, it should be understood that the present invention comprehends not only decoyants based on the cholinergic binding site but decoyants based on any endogenous receptor for a foreign agent which exerts an undesired effect only after binding to that endogenous receptor. The first requirement of a decoyant in accordance with the present invention is that it be a mimic of the endogenous receptor, i.e., it must functionally resemble the binding site, although it may differ physically. The term "functionally resemble" means that the decoyant binds to the foreign agent in question in a selective and specific manner and with reasonable affinity. For the purpose of this invention, a receptor can be any ligand-binding molecule as, for example, the ligand-binding site of a traditional cell-surface receptor, the substrate binding site of an enzyme, the ligand-binding site of gangliosides, etc.

It must be understood, however, that a decoyant in accordance with the present invention cannot be an immunoglobulin nor can it be derived from immunoglobulins. While it is true that an immunoglobulin directed against the "binding domain" of a-pathogen could generally function as a decoy, such is not intended to be included within the concept of the present invention.

A decoyant in accordance with the present invention should not be substantially immunogenic. Reduction of size is a means of diminishing the immunogenicity of a substance, but not all large molecules are as immunogenic as some small molecules. To be classified as a decoyant in accordance with the present invention, the substance must be substantially non-immunogenic in the system of the host, regardless of the size of the substance, although the smallest possible size is preferred. It is very important, however, that the decoyant not be sufficiently immunogenic to elicit an autoimmune response against the endogenous receptor when administered in vivo. In the case of the cholinergic receptor, such an autoimmune response might cause a case of myasthenia gravis.

A decoyant in accordance with the present invention must comprise the essential elements of the binding site of a receptor and not substantially more. For the purpose of this invention, the "essential elements" of a binding site are defined as those elements essential for the decoyant activity, i.e., ligand recognition and binding. A receptor consists of many residues, only a few of which are involved in ligand recognition and binding. However, as discussed above, the decoyants of the present invention may be further modified for purposes of drug design. Thus, for example, the entire α-subunit of AcChoR would not qualify as a decoyant, being both immunogenic and also considerably longer than necessary. The α-subunit does, however, contain the potential information needed for the design and construction of a decoyant, i.e., sequence α-184-200. The fact that some additional peptide units may also be present, for example to improve the solubility of the essential required sequence, would not remove the structure from the category of decoyant as long as it is still substantially non-immunogenic and it is still selective, specific and of reasonable affinity. Addition of sugar molecules could be a modification with the same effect. Thus, additions to the molecule for the purpose of drug design are not considered when determining whether the substance contains substantially more than the elements of the endogenous receptor which are required for binding to the foreign agent in question.

As previously indicated, a decoyant must be selective, specific and of reasonable affinity with respect to the agent for which it is designed. Thus, for example, mannose, a simple sugar, may interfere with infection by bacteria that have type-I mannose specific pili; however, the selectivity of mannose is not sufficient and neither is its affinity.

A decoyant is a drug designed to intercept an invading foreign agent having an undesired effect. Such foreign agents may include toxins, poisons, bacteria, viruses, including retroviruses, etc. As long as the foreign agent exerts its pathogenic or toxic effect (or any other effect which is desired to be eliminated) only after binding to a receptor site somewhere in the host, a decoyant can be designed in accordance with the present invention to prevent such binding and thereby eliminate such undesired effect. Once the procedures of the present invention are known, as well as the fact that such receptor fractions containing ligand binding sites will still competitively bind the ligands in vivo, those of ordinary skill in the art will understand that decoyants derived from other receptors, designed to bind to other pathogenic agents and toxins, can be obtained using no more than routine experimentation.

Among the pathogenic agent-receptor pairs for which decoyants can readily be obtained in accordance with the present invention is the T-cell surface glycoprotein CD4 (T4), which is the cellular receptor for human immunodeficiency virus, type 1 (HIV-1), the first member of the family of viruses that cause acquired immunodeficiency syndrome (AIDS). The infection of the HIV virus starts through the binding of its envelope protein (gp120) to the T4 receptor (CD4) located on the T4 lymphocytes. It has recently been confirmed that soluble, secreted forms of CD4 can be used to competitively bind HIV-1 and thus neutralize the infectivity of HIV-1 (Smith et al, "Blocking of HIV-1 Infectivity by a Soluble, Secreted Form of the CD4 Antigen", Science, 238, 1704–1707 (1987)). Intact CD4 would not be a decoyant in accordance with the present invention in view of its size. It does, however, contain the essence for a decoyant. The minimal binding domain of CD4 can be identified using no more than routine experimentation by the means described herein for arriving at the minimal binding domain for the cholinergic receptor, e.g., by means of proteolysis and protein blotting followed by recombinant DNA procedures.

Another ligand-receptor pair particularly suited for the preparation of decoyants in accordance with the present invention is organophosphate-acetylcholine esterase. Such a decoy would relieve some of the effects of nerve gas. Other examples are LSD and the serotonin receptor and strychnine and the glycine receptor.

Table 3 shows additional ligand-receptor pairs for which decoyants in accordance with the present invention can be designed using no more than routine experimentation:

TABLE 3

| Ligand | Receptor |
| --- | --- |
| Calcium | 28 kDa of bovine cerebellum and kidney |
|  | Calmodulin |
| Heparin | apoE and apoB of human plasma |
| Pili of Gonococcus | 14 and 16 kDa proteins of CHO cells |
| Virus |  |
| Retrovirus type 3 | 67 kDa glycoprotein of rodent lymphoid and neuronal cells |
| Sendai virus | Human erythrocyte glycophorin |
| Potato spindle tuber viroid | Nuclear proteins |

The decoyants of the present invention may be administered to an animal, including a human patient, in order to ameliorate the undesired effects of the foreign agent for which it was designed. Such decoyants can be used not only for the treatment of humans, but also for the treatment of other animals, including mammals, poultry, fish, etc. Furthermore, decoyants in accordance with the present invention could be designed for the protection or treatment of plants. The specific effective dosages for the treatment of any given foreign agent can readily be empirically determined by those of ordinary skill in the art without undue experimentation. However, those skilled in the art will understand that the dosage of decoyant will depend to some extent on the amount of foreign agent in the system of the host. The ratio of decoyant to foreign agent molecules is preferably in the range of 1:1 to 1:10. Animal tests have shown that a large excess of decoyant is not necessary for effectiveness. Preferably, the amount of foreign agent in the bloodstream of the host will be monitored and the decoyant dosage adjusted accordingly during the course of treatment.

Compositions within the scope of the present invention include compositions wherein the decoyant is present in an effective amount to achieve its intended purpose. Determination of the effective amounts is within the skill in the art.

In addition to the decoyants of the present invention, the pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered by injection, contain from about 0.1 to 99 percent, and preferably from about 25 to 85 percent by weight, of the active ingredient, together with the excipient.

Any conventional route of administration may be used for the decoyants of the present invention. Although the preferred mode of administration is by injection, e.g., intravenously, intradermally, intraperitoneally, etc, they may also be administered orally, by suppository or by any other route.

Other non-conventional means of administration can be envisioned which are also intended to be comprehended within the scope of the present invention. For example, while the present system for the expression of the active ingredient by bacteria involves the bacterial expression vector pATH2, other bacterial expression systems exist which actually secrete the expressed protein into the medium. It could be contemplated that such a secreting expression system could be used to generate the decoyant from within the host rather than producing it ex vivo and administering it to the host. Obviously, the secreting system must be compatible with the host. The term "administration" as used in the present specification and claims is intended to include such in vivo secretion systems.

The pharmaceutical preparations of the present invention are manufactured in a manner which is itself known, for example, by means of conventional mixing, dissolving, or lyophilizing processes. Suitable formulations for parenteral administration include aqueous solutions of the active compounds in water-soluble form. In addition, suspensions of the active compounds as appropriate oily injection suspensions may be administered. Suitable lipophilic solvents or vehicles include fatty oils such as sesame oil, or synthetic fatty acid esters such as ethyl oleate or triglycerides. Aqueous injection suspensions may contain substances which increase the viscosity of the suspension such as sodium carboxymethyl cellulose, sorbitol, and/or dextran. optionally, the suspension may also contain stabilizers. The decoyants of the present invention may also be administered in the form of liposomes, pharmaceutical compositions in which the active ingredient is contained either dispersed or variously present in corpuscles.consisting of aqueous concentric layers adherent to lipidic layers. The active ingredient may be present both in the aqueous layer and in the lipidic layer, or, in any event, in the non-homogeneous system generally known as a liposomic suspension.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology and terminology employed herein is for the purpose of description and not of limitation.

I claim:

1. A method for the treatment of an organism which has been subjected to a foreign agent which exerts an undesired effect only after first binding to an endogenous receptor, said treatment being for the amelioration of said undesired effect, comprising:

administering to said organism, in a quantity sufficient to ameliorate said undesired effect of said foreign agent, a molecular decoyant having a chemical structure which functionally resembles the ligand binding site of said endogenous receptor for the foreign agent, said decoyant being a substance selected from the group consisting of:

(1) a substance which is a portion of a natural receptor for said foreign agent, said portion being (a) sufficiently small so as not to elicit an autoimmune response against the endogenous receptor when administered in vivo, and (b) not substantially larger than the smallest size needed to retain the elements of the binding site of said natural receptor which are essential for retaining the ability of said receptor to selectively and specifically recognize and bind to said foreign agent with an affinity permitting competition with binding of said foreign agent to said endogenous receptor;

(2) a substance having a chemical structure which substantially corresponds to that of said substance of (1), synthesized by chemical and/or recombinant DNA techniques and having the ability to selectively and specifically recognize and bind of the foreign agent without eliciting an autoimmune response against the endogenous receptor when administered in vivo; and (3) a substance having a chemical structure consisting essentially of the chemical structure of the substance of (1) or (2).

2. A method in accordance with claim 1, wherein the foreign agent is a snake venom toxin.

3. A method in accordance with claim 1, wherein the foreign agent is a rabies virus.

4. A method in accordance with claim 1, wherein the foreign agent is HIV virus.

5. A method in accordance with claim 1, wherein said foreign agent is an HIV virus and said endogenous receptor is the T4 cell antigen of lymphocytes.

6. A method in accordance with claim 1, wherein said molecular decoyant is a substance of (1).

7. A method in accordance with claim 1, wherein said molecular decoyant is a peptide chain expressed by cells genetically engineered by recombinant DNA techniques.

8. A method in accordance with claim 1, wherein said molecular decoyant is a synthetic peptide.

9. A method in accordance with claim 1, wherein said organism is an animal.

10. A method in accordance with claim 9, wherein said animal is a human.

11. A method in accordance with claim 1, wherein said decoyant is a substance of (1) or a substance having the same chemical structure as a substance of (1) synthesized by chemical and/or recombinant DNA techniques.

12. A method in accordance with claim 11, wherein said molecular decoyant is a peptide chain expressed by cells genetically engineered by recombinant DNA techniques.

13. A method in accordance with claim 11, wherein said molecular decoyant is a synthetic peptide.

14. A method in accordance with claim 1, wherein said substance of (2) has the same chemical structure as the substance of (1) synthesized by chemical and/or recombinant DNA techniques.

15. A method for the treatment of an organism which has been subjected to a foreign agent which exerts an undesired effect only after first binding to an endogenous receptor, said treatment being for the amelioration of said undesired effect, comprising:

administering to said organism, in a quantity sufficient to ameliorate said undesired effect of said foreign agent, a molecular decoyant having a chemical structure which functionally resembles the ligand binding site of said endogenous receptor for the foreign agent, said decoyant being a substance selected from the group consisting of:
(1) a substance which is a portion of a natural receptor for said foreign agent, said portion being (a) sufficiently small so as not to elicit an autoimmune response against the endogenous receptor when administered in vivo, and (b) not substantially larger than the smallest size needed to retain the elements of the binding site of said natural receptor which are essential for retaining the ability of said receptor to selectively and specifically recognize and bind to said foreign agent with an affinity permitting competition with binding of said foreign agent to said endogenous receptor;
(2) a substance having a chemical structure which substantially corresponds to that of said substance of (1), synthesized by chemical and/or recombinant DNA techniques and having the ability to selectively and specifically recognize and bind to the foreign receptor without eliciting an autoimmune response against the endogenous receptor when administered in vivo; and
(3) a substance having a chemical structure consisting essentially of the chemical structure of the substance of (1) or (2);
with the proviso that said endogenous receptor is not the CD4 receptor.

16. A method for the treatment of an organism which has been subjected to a curarimimetic neurotoxin, which neurotoxin exerts an undesired effect only after first binding to a cholinergic receptor, said treatment being for the amelioration of said undesired effect, comprising:
administering to said organism, in a quantity sufficient to ameliorate said undesired effect of said curarimimetic neurotoxin, a molecular decoyant having a chemical structure which functionally resembles the ligand binding site of said cholinergic receptor, said decoyant being a substance selected from the group consisting of:
(1) a substance which is a portion of a natural cholinergic receptor, said portion being (a) sufficiently small so as not to elicit an autoimmune response against the endogenous receptor when administered in vivo, and (b) not substantially larger than the smallest size needed to retain the elements of the binding site of said natural receptor which are essential for retaining the ability of said receptor to selectively and specifically recognize and bind to said curarimimetic neurotoxin with an affinity permitting competition with binding of said curarimimetic neurotoxin to said cholinergic receptor;
(2) a substance having a chemical structure which substantially corresponds to that of said substance of (1), synthesized by chemical and/or recombinant DNA techniques and having the ability to selectively and specifically recognize and bind to the curarimimetic neurotoxin without eliciting an autoimmune response against the endogenous receptor when administered in vivo; and
(3) a substance having a chemical structure consisting essentially of the chemical structure of substance (1) or (2).

17. A method in accordance with claim 16, wherein said foreign agent is α-bungarotoxin, cobratoxin, d-tubocurarine, decamethonium, or rabies-virus, and said endogenous receptor is the nicotinic acetylcholine receptor.

18. A method in accordance with claim 16, wherein said molecular decoyant includes the amino acid sequence Trp-Lys-His-Trp-Val-Tyr-Tyr-Thr-Cys-Cys-Pro-Asp-Thr-Pro-Tyr-Leu-Asp, which molecular decoyant has the ability of selectively and specifically recognizing and binding to curarimimetic neurotoxin.

19. A method in accordance with claim 16, wherein said molecular decoyant includes an amino acid sequence substantially corresponding to Trp-Lys-His-Trp-Val-Tyr-Tyr-Thr-Cys-Cys-Pro-Asp-Thr-Pro-Tyr-Leu-Asp, which molecular decoyant has the ability of selectively and specifically recognizing and binding to curarimimetic neurotoxin.

20. A method for the treatment of an organism which has been subjected to a foreign agent which exerts an undesired effect only after first binding to an endogenous receptor, said treatment being for the amelioration of said undesired effect, comprising:
administering to said organism, in a quantity sufficient to ameliorate said undesired effect of said foreign agent, a molecular decoyant which is a substance selected from the group consisting of:
(1) a substance which is a portion of a natural receptor for said foreign agent, said portion being not substantially larger than the smallest size needed to retain the elements of the binding site of said natural receptor which are essential for retaining the ability of said receptor to selectively and specifically recognize and bind to said foreign agent with an affinity permitting competition with binding of said foreign agent to said endogenous receptor;
(2) a substance having a chemical structure which substantially corresponds to that of said substance of (1), synthesized by chemical and/or recombinant DNA techniques and having the ability to selectively and specifically recognize and bind to the foreign agent with an affinity permitting competition with binding of said foreign agent to said endogenous receptor; and
(3) a substance having a chemical structure consisting essentially of the chemical structure of the substance of (1) or (2).

21. A method in accordance with claim 20, wherein said decoyant is a substance of (1) or a substance having the same chemical structure as a substance of (1) synthesized by chemical and/or recombinant DNA techniques.

22. A method in accordance with claim 20, wherein said substance of (2) has the same chemical structure as the substance of (1) synthesized by chemical and/or recombinant DNA techniques.

23. A method for the treatment of an organism which has been subjected to a curarimimetic neurotoxin, which neurotoxin exerts an undesired effect only after first binding to a cholinergic receptor, said treatment being for the amelioration of said undesired effect, comprising:
administering to said organism, in a quantity sufficient to ameliorate said undesired effect of said curarimimetic neurotoxin, a molecular decoyant which is a substance selected from the group consisting of:
(1) a substance which is a portion of a natural cholinergic receptor, said portion being not substantially larger than the smallest size needed to retain the elements of the binding site of said natural receptor which are essential for retaining the ability of said receptor to selectively and specifically recognize and bind to said curarimimetic neurotoxin with an affinity permitting competition with binding of said curarimimetic neurotoxin to said cholinergic receptor;

(2) a substance having a chemical structure which substantially corresponds to that of said substance of (1), synthesized by chemical and/or recombinant DNA techniques and having the ability to selectively and specifically recognize and bind to the curarimimetic neurotoxin with an affinity permitting competition with binding of said curarimimetic neurotoxin to said cholinergic receptor; and (3) a substance having a chemical structure consisting essentially of the chemical structure of substance (1) or (2).

24. A method in accordance with claim 23, wherein said decoyant is a substance of (1) or a substance having the same chemical structure as a substance of (1) synthesized by chemical and/or recombinant DNA techniques.

25. A method in accordance with claim 23, wherein said substance of (2) has the same chemical structure as the substance of (1) synthesized by chemical and/or recombinant DNA techniques.

26. A method in accordance with claim 23, wherein said molecular decoyant includes the amino acid sequence Trp-Lys-His-Trp-Val-Tyr-Tyr-Thr-Cys-Cys-Pro-Asp-Thr-Pro-Tyr-Leu-Asp, which molecular decoyant has the ability of selectively and specifically recognizing and binding to curarimimetic neurotoxin.

* * * * *

UNITED STATES PATENT AND TRADEMARK OFFICE
CERTIFICATE OF CORRECTION

PATENT NO. : 5,770,572
DATED : Jun. 23, 1998
INVENTOR(S) : Gershoni

It is certified that error appears in the above-identified patent and that said Letters Patent is hereby corrected as shown below:

Col. 2, line 19, delete "a-method" and insert therefor --a method--;

Col. 3, line 14, delete "Pi" and insert therefor --$P_1$--;

Col. 5, line 19, delete "sci." and insert therefor --Sci.--; and

Col. 6, line 11, delete "=1.2X" and insert therefor --=1.2X--.

Signed and Sealed this

Fifteenth Day of September, 1998

Attest:

BRUCE LEHMAN

*Attesting Officer*     *Commissioner of Patents and Trademarks*